(12) United States Patent
Matus (10) Patent No.: US 11,224,337 B2
(45) Date of Patent: Jan. 18, 2022

(54) OROPHRANGEAL GLOVE FOR USE WITH A RIGID BRONCHSCOPE AND A METHOD

(71) Applicant: Ismael A. Matus, Landenberg, PA (US)

(72) Inventor: Ismael A. Matus, Landenberg, PA (US)

(73) Assignee: Skillhead LLC, Buford, GA (US)

( * ) Notice: Subject to any disclaimer, the term of this patent is extended or adjusted under 35 U.S.C. 154(b) by 409 days.

(21) Appl. No.: 16/045,396

(22) Filed: Jul. 25, 2018

(65) Prior Publication Data

US 2020/0029800 A1     Jan. 30, 2020

(51) Int. Cl.
*A61B 1/267* (2006.01)
*A61B 1/00* (2006.01)
*A61M 16/04* (2006.01)

(52) U.S. Cl.
CPC ........ *A61B 1/2676* (2013.01); *A61B 1/00147* (2013.01); *A61M 16/0402* (2014.02); *A61M 16/0497* (2013.01)

(58) Field of Classification Search
CPC ............ A61B 1/267–2736; A61B 1/24; A61B 1/00147; A61B 17/24; A61B 2017/242; A61M 16/04–0402; A61M 16/0486–0497
USPC ....... 128/200.26, 207.14; 600/101, 120, 185, 600/190, 194
See application file for complete search history.

(56) References Cited

U.S. PATENT DOCUMENTS

| | | | | |
|---|---|---|---|---|
| 3,543,751 A | * | 12/1970 | Sheffer | A61M 16/0488 128/207.15 |
| 4,231,365 A | * | 11/1980 | Scarberry | A61M 16/0445 128/207.15 |
| 4,270,531 A | | 6/1981 | Blachly et al. | |
| 4,681,094 A | * | 7/1987 | Rolnick | A61B 1/06 600/185 |
| 5,590,643 A | | 1/1997 | Flam | |
| 5,623,924 A | | 4/1997 | Lindenman et al. | |
| 6,386,199 B1 | * | 5/2002 | Alfery | A61M 16/04 128/207.15 |
| 8,104,467 B2 | | 1/2012 | Napier | |
| 8,752,555 B2 | | 6/2014 | Goldsby | |

(Continued)

FOREIGN PATENT DOCUMENTS

GB        2170106      7/1986
WO    2016023747      2/2016

*Primary Examiner* — Elliot S Ruddie
(74) *Attorney, Agent, or Firm* — Smith Tempel Blaha LLC; Daniel J. Santos (57) ABSTRACT

An oropharyngeal glove for use with a rigid bronchoscope is provided for use during a rigid bronchoscopy procedure. When the oropharyngeal glove is in its installed state, it conforms to the patient's mouth and throat. The oropharyngeal glove includes upper and lower teeth guards that protect the patient's upper and lower front teeth, respectively, when the glove is in the installed state. A first opening is formed in the oropharyngeal glove in its proximal end that allows the rigid bronchoscope to enter glove. The oropharyngeal glove has a second opening formed in its distal end through which the rigid bronchoscope passes to enter the patient's trachea. The portions of the glove that conform to the patient's mouth and throat comprise a protective lining that protects the mouth, throat and vocal cords from being damaged by the rigid bronchoscope.

18 Claims, 6 Drawing Sheets

(56) References Cited

U.S. PATENT DOCUMENTS

| | | |
|---|---|---|
| 9,307,891 B2 | 4/2016 | Carter et al. |
| 9,649,462 B2 | 5/2017 | Franckowiak |
| 2014/0150782 A1* | 6/2014 | Vazales ............. A61M 16/0434 128/202.16 |
| 2015/0165148 A1 | 6/2015 | Kozlowski |

* cited by examiner

OROPHRANGEAL GLOVE FOR USE WITH A RIGID BRONCHSCOPE AND A METHOD

BACKGROUND

Bronchoscopy is an endoscopic process that involves visualizing the inside of the airways for therapeutic and diagnostic purposes. An instrument known as a bronchoscope is inserted through the patient's mouth into the airways to allow the physician to examine the airways for abnormalities such as bleeding, tumors or inflammation, for example.

Generally, there are two types of bronchoscopes: flexible bronchoscopes and rigid bronchoscopes. Flexible bronchoscopes have a fiber optic system that transmits an image from the end of an optical fiber that is inside of the patient to an eyepiece or camera at the opposite end of the optical fiber. Rigid bronchoscopes have a larger lumen than that of the flexible bronchoscope and are typically made of a hard metallic material.

There are problems that can occur when performing rigid bronchoscopy. Because of the rigid nature of the instrument, it can sometimes cause abrasions or lacerations to the patient's mouth, throat or vocal cords and can damage the patient's teeth.

Also, as rigid bronchoscopic procedures are performed under general anesthesia and are considered "open circuit" procedures, varying degrees of air leaks exist not only through the barrel of the rigid bronchoscope to the atmosphere, but also from the patient's airway around the rigid bronchoscope which can challenge ventilation of the patient.

A need exists for a medical device and a method that can be used when performing rigid bronchoscopy to protect the patient's mouth, throat, vocal cords and teeth and that reduce air leakage.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

The inventive principles and concepts are directed to an oropharyngeal glove for use with a rigid bronchoscope. When the oropharyngeal glove is in its installed state, it conforms to the patient's mouth and throat. The oropharyngeal glove includes upper and lower teeth guards that are in contact with the patient's upper and lower front teeth, respectively, when the oropharyngeal glove is in the installed state. The oropharyngeal glove has a first opening formed in its proximal end that allows the rigid bronchoscope to enter the oropharyngeal glove. The oropharyngeal glove has a second opening formed in its distal end through which the rigid bronchoscope passes to enter the patient's trachea. The portions of the oropharyngeal glove that conform to the patient's mouth and throat comprise a protective lining that protects the mouth, throat and vocal cords from being damaged by the rigid bronchoscope. The upper and lower teeth guards protect the patient's upper and lower front teeth, respectively, from being damaged by the rigid bronchoscope during the bronchoscopy procedure and during installation and removal of the bronchoscope.

Figure 1:
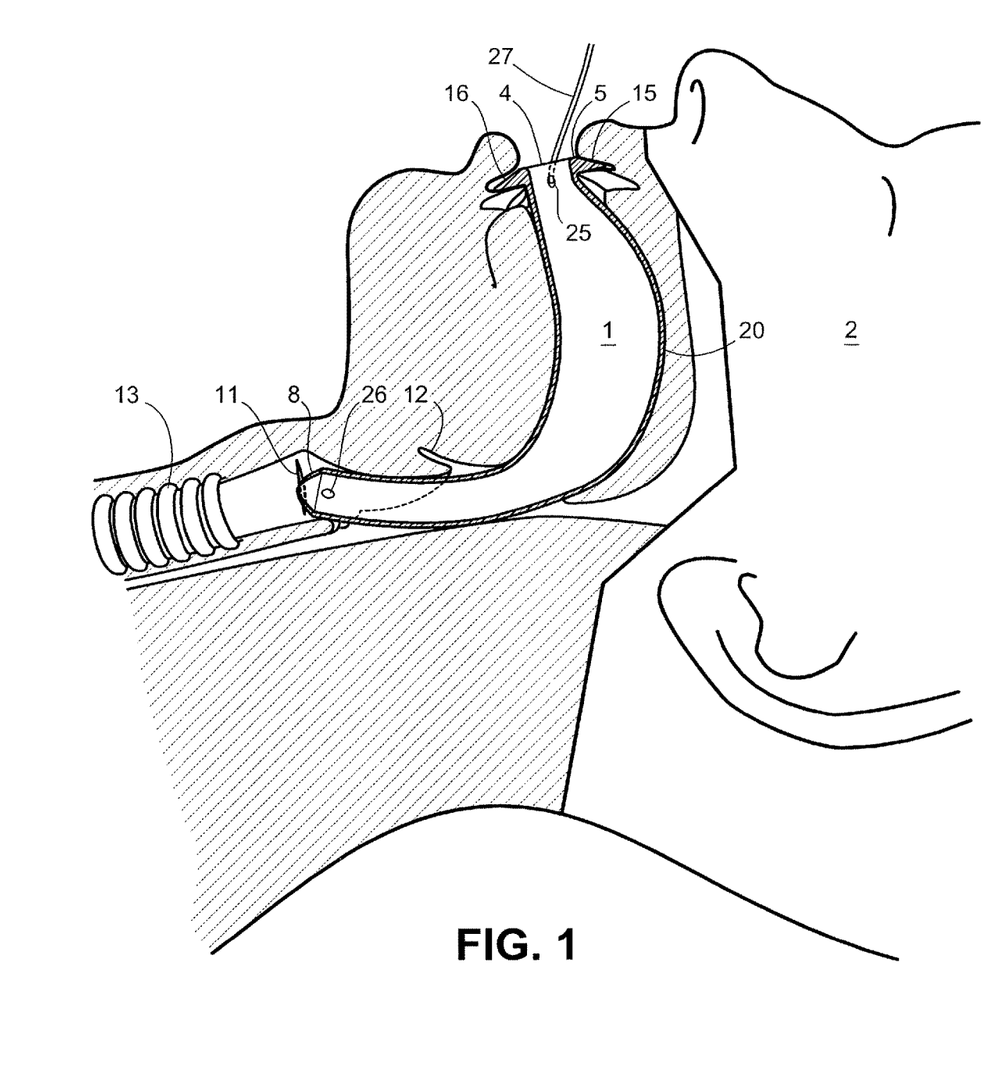
FIG. 1 is a side transparency view of a patient with an oropharyngeal glove installed in the patient's mouth and throat.
Figure 2:
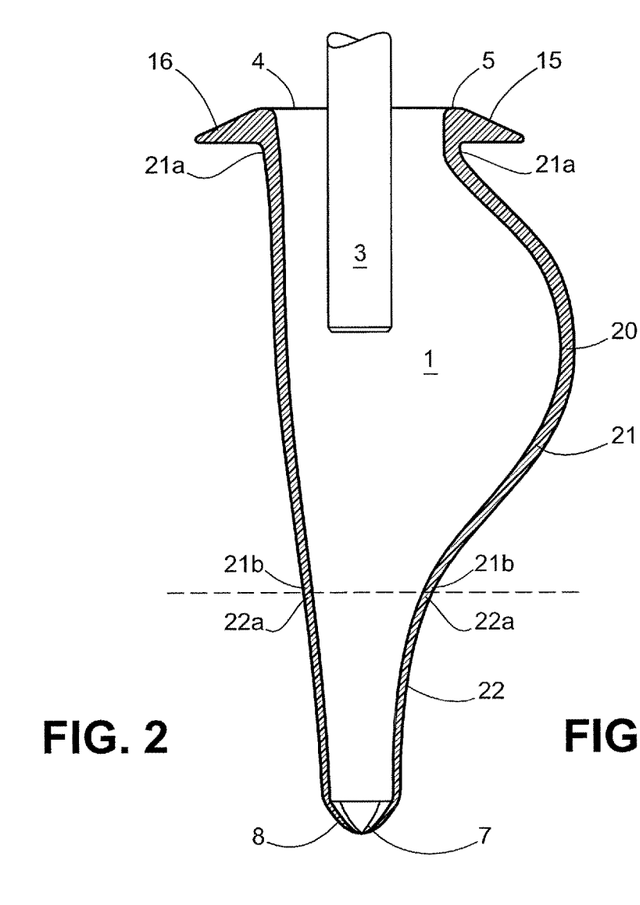
FIG. 2 is a side cross-sectional view of the oropharyngeal glove shown in FIG. 1 in its uninstalled state and having a generally tubular portion of a rigid bronchoscope inserted through a first opening formed in a proximal end of the oropharyngeal glove.
Figure 3:
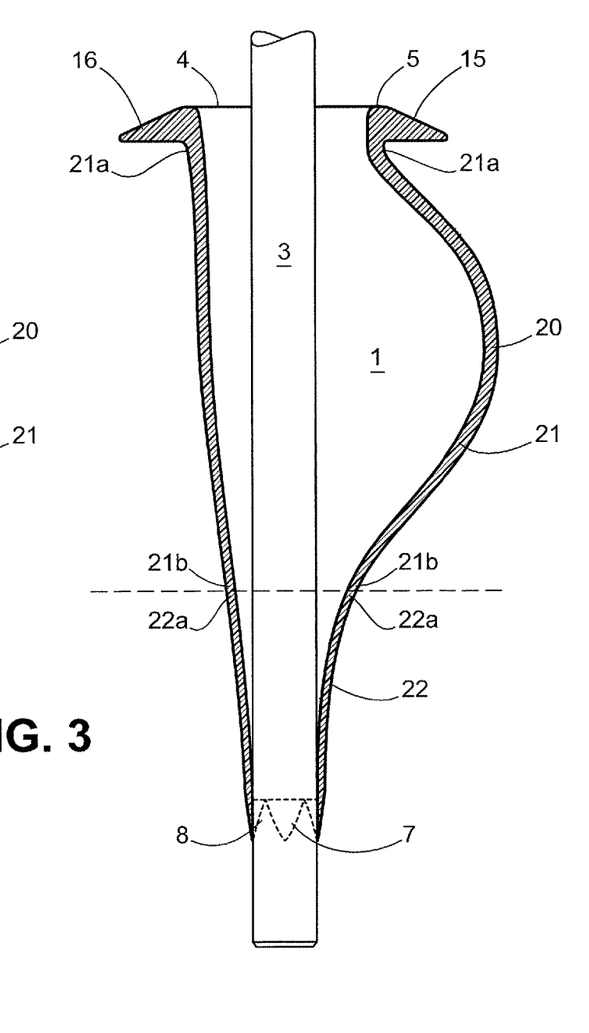
FIG. 3 is a side cross-sectional view of the oropharyngeal glove shown in FIG. 1 in its uninstalled state as show in FIG. 2 and having the generally tubular portion of a rigid bronchoscope shown in FIG. 2 passing through a slit opening formed in a distal end of the oropharyngeal glove.
Figure 4:
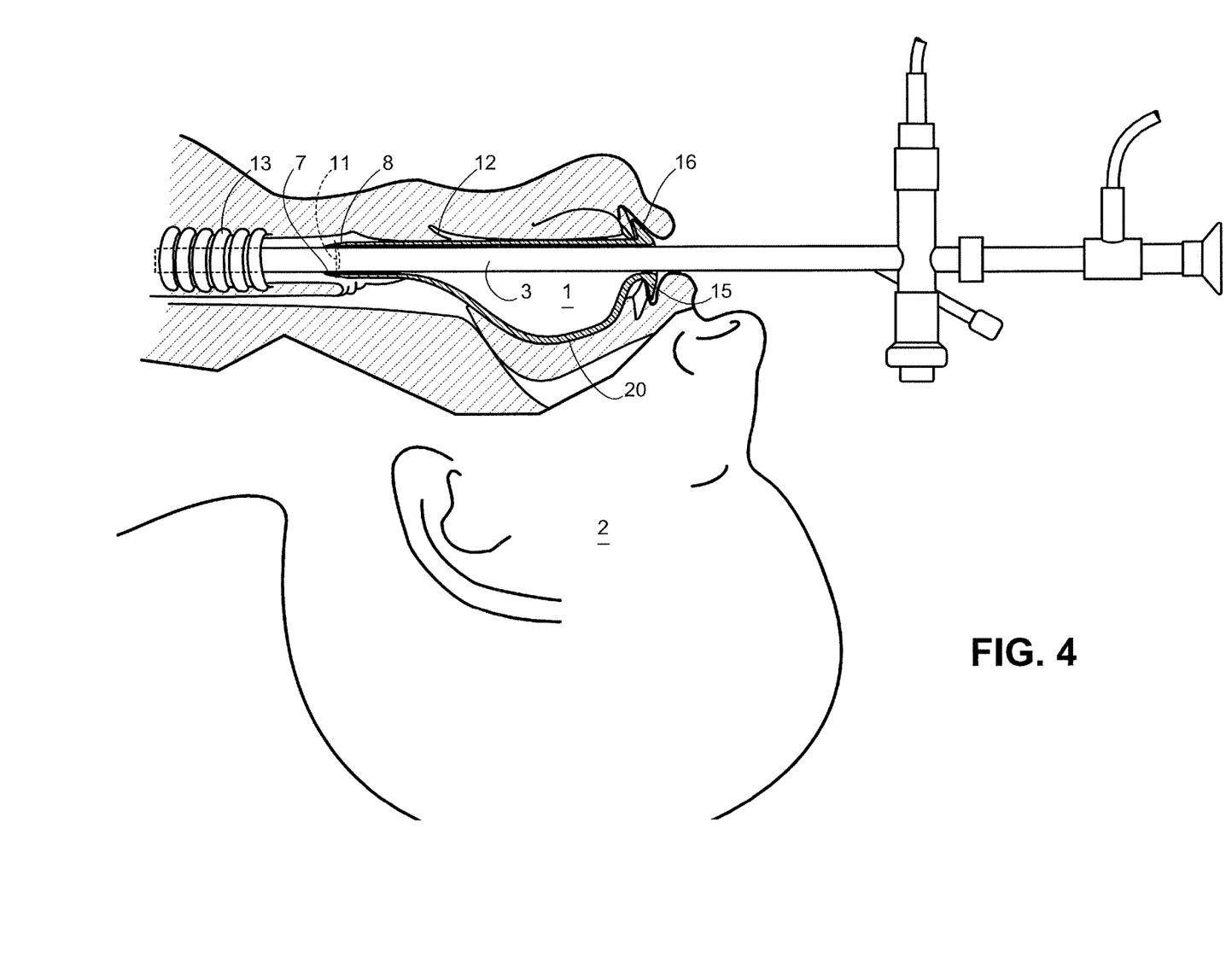
FIG. 4 is a side transparency view of a patient with the oropharyngeal glove installed in the patient's mouth and throat with a generally tubular portion of a rigid bronchoscope passing through the oropharyngeal glove from the proximal end thereof through a second opening formed in the distal end thereof into the patient's trachea.

FIG. 1 is a side transparency view of a patient 2 with the oropharyngeal glove 1 in accordance with a representative embodiment installed in the patient's mouth and throat. FIG. 2 is a side cross-sectional view of the oropharyngeal glove 1 shown in FIG. 1 in its uninstalled state and having a generally tubular portion 3 of a rigid bronchoscope inserted through a first opening 4 formed in a proximal end 5 of the oropharyngeal glove 1. FIG. 3 is a side cross-sectional view of the oropharyngeal glove shown in FIG. 1 in its uninstalled state as shown in FIG. 2 with the generally tubular portion 3 of a rigid bronchoscope passing through a second opening 7 formed in a distal end 8 of the oropharyngeal glove 1. FIG. 4 is a side transparency view of the patient 2 with the oropharyngeal glove 1 installed in the patient's mouth and throat with the generally tubular portion 3 of the rigid bronchoscope passing through the oropharyngeal glove 1 from the proximal end 5 thereof through the second opening 7 formed in the distal end 8 thereof into the patient's trachea 13.

In the installed state of the oropharyngeal glove 1, the distal end 8 preferably is positioned just above, or flush with, the vocal cords 11 and below the epiglottis 12. In other words, in the installed state of the oropharyngeal glove 1, the distal end 8 preferably is positioned flush with the vocal cords 11 or in between the vocal cords 11 and the epiglottis 12. In this position, the second opening 7 formed in the distal end 8 is aligned with the trachea 13 and the oropharyngeal glove 1 blocks the entryway of the esophagus.

The oropharyngeal glove 1 has upper and lower teeth guards 15 and 16, respectively, that are in contact with the patient's upper and lower front teeth, respectively, when the oropharyngeal glove 1 is in the installed state shown in FIG. 1. The oropharyngeal glove 1 has a flexible body 20 that extends from the upper and lower teeth guards 15 and 16, respectively, to the distal end 8 of the oropharyngeal glove. The flexible body 20 is configured to conform to a patient's mouth and throat when the oropharyngeal glove 1 is installed in the patient's mouth and throat such that outer walls of the flexible body 20 are in contact with the patient's tongue, with the inner walls of the patient's cheeks, with the roof of the patient's mouth, and with the patient's throat. Preferably, the outer surface of the flexible body 20 forms an airtight, or nearly airtight, seal with these anatomical features of the patient's mouth and throat.

In accordance with a representative embodiment, the flexible body 20 of the oropharyngeal glove 1 comprises a first membrane portion 21 (FIGS. 2 and 3) and a second membrane portion 22 (FIGS. 2 and 3). The first membrane portion 21 has a first end 21a that meets the upper and lower teeth guards 15 and 16, respectively. The teeth guards 15 and 16 and the first end 21a of the first membrane portion 21 define the first opening 4. The first membrane portion 21 has a second end 21b that meets a first end 22a of the second membrane portion 22. The second membrane portion 22 has a second end 22b that meets the distal end 8 of the oropharyngeal glove 1. The term "meets," as that term is used herein, can have multiple meanings. The term "meets" can mean that there is a physical joining of different elements or features of different materials, a contiguous transition of one element or feature into another element or feature made of the same material based on a preselected or arbitrary boundary, a joining of different elements or features via an attachment mechanism, such as an adhesive material, for example, etc.

When the oropharyngeal glove 1 is installed in a patient's mouth and throat, as shown in FIG. 1, outer walls of the first membrane portion 21 are in contact with the patient's tongue, with the inner walls of the patient's cheeks and with the roof of the patient's mouth, and outer walls of the second membrane portion 22 are in contact with the patient's throat. As indicated above, this contact preferably forms an airtight, or nearly airtight, seal.

In accordance with a representative embodiment, in the installed and uninstalled states, the first membrane portion 21 has a width, or circumference, that is greater than a width, or circumference, of the second membrane portion 22. The reason for this is that the inside of the mouth is wider than the inside of the throat. The first and second membrane portions 21 and 22, respectively, are flexible to allow the oropharyngeal glove 1 to be bent, folded or compressed while it is being installed in the patient's mouth or throat. The person performing the bronchoscopy procedure may install the oropharyngeal glove 1 by hand or by using a tool (not shown) to temporarily deform the oropharyngeal glove 1 to enable it to be inserted into the proper position shown in FIG. 1. The oropharyngeal glove 1 is made of a material that has some memory so that the oropharyngeal glove 1 attempts to return to the state it was in before being temporarily deformed. In the installed state of the oropharyngeal glove 1 shown in FIG. 1, the second membrane portion 22 blocks the entryway of the esophagus of the patient and the outer surfaces of the first and second membrane portions 21 and 22, respectively, create an airtight, or nearly airtight, seal with the surfaces of the mouth and throat, respectively.

In accordance with a representative embodiment, the oropharyngeal glove 1 includes at least a first oxygen port 25 (FIG. 1) disposed at the proximal end 5 of the oropharyngeal glove 1 and at least a second oxygen port 26 (FIG. 1) disposed at the distal end 8 of the oropharyngeal glove 1. The first and second oxygen ports 25 and 26, respectively, are interconnected via a conduit disposed in the walls of the flexible body 20. Oxygen may be delivered via a tube 27 to the first oxygen port 25. Oxygen delivered to the first oxygen port 25 will flow through the conduit to the second oxygen port 26. During the bronchoscopy procedure, oxygen received in the oxygen port 26 from the first oxygen port 25 will flow out of the second oxygen port 26 near the entryway of the trachea 13, thereby providing additional oxygen to the patient's lungs.

In accordance with a representative embodiment, the second opening 7 (FIGS. 2 and 3) is a slit opening, as depicted in FIGS. 2-4. The slit opening opens just wide enough to allow the tubular portion 3 of the rigid bronchoscope to pass through it and forms a tight friction fit about the tubular portion 3. The friction fit is tight enough to substantially seal the slit opening to prevent air from passing through the opening.

In accordance with an embodiment, the oropharyngeal glove 1 is an integrally-formed part, although the oropharyngeal glove 1 could comprise separate parts that are joined together by some suitable process and mechanism. The oropharyngeal glove 1 may be made of any suitable material, such as a medical-grade plastic or a synthetic rubber, for example. In any case, the upper and lower teeth guards 15 and 16, respectively, will typically be the hardest and least flexible elements of the oropharyngeal glove 1, which can be accomplished by making those elements thicker and/or denser than any of the other elements. The first and second membrane portions 21 and 22, respectively, could be made of the same material (e.g., medical-grade plastic or rubber), but with the second membrane portion 22 being more flexible than the first membrane portion 21. The first and second membrane portions 21 and 22 can also be made of different materials. This can be accomplished in a number of ways, such as, for example, by making the walls of the second membrane portion 22 thinner than the walls of the first membrane portion 21. This is demonstrated in FIGS. 2 and 3, which show that the walls of the flexible body 20 in the first membrane portion 21 are thicker than the walls of the flexible body 20 in the second membrane portion 22.

Persons of skill in the art will understand, in view of the considerations described herein, how to select a suitable material and manufacturing process to form the oropharyngeal glove 1 to have the desired characteristics of flexibility, conformity and strength. For example, a plastic molding process can be used to form the oropharyngeal glove 1 as an integrally-formed, or unitary, part. As another example, an epoxy replication process may be used to form the oropharyngeal glove 1. As indicated above, the oropharyngeal glove 1 may be made of different materials. For example, the oropharyngeal glove 1 may be made of plastic and rubber. Thus, the inventive principles and concepts are not limited with respect to the material(s) that is used to make the oropharyngeal glove 1 or with respect to the process that is used to make the oropharyngeal glove 1, as will be understood by those of skill in the art in view of the description provided herein.

Figure 5:
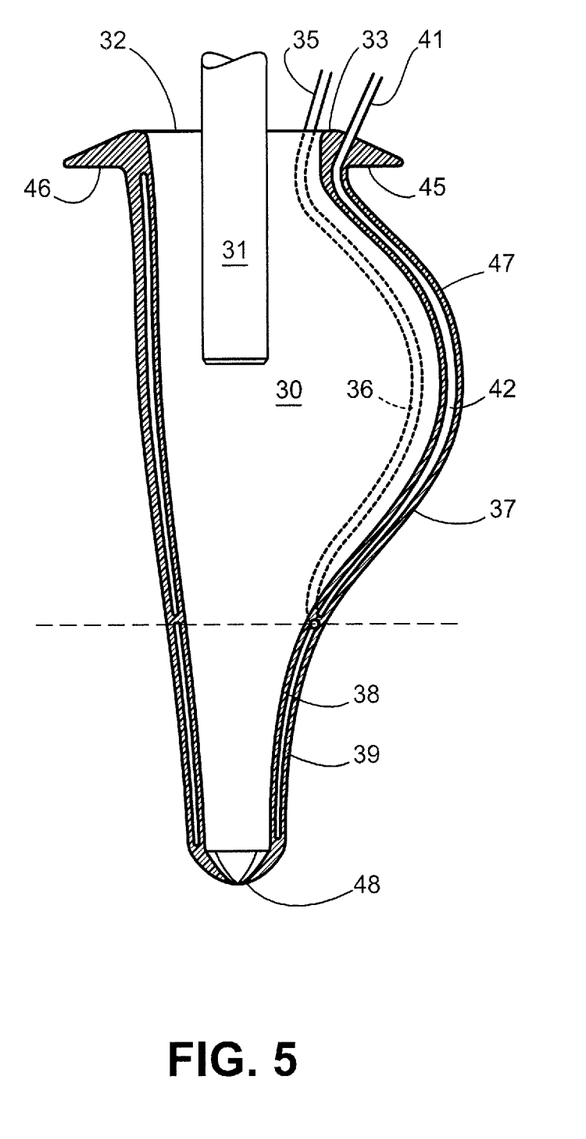
FIG. 5 is a side cross-sectional view of an inflatable oropharyngeal glove in accordance with another embodiment in its uninstalled state, and with a generally tubular portion of a rigid bronchoscope through an opening formed in a proximal end of the glove.

FIG. 5 is a side cross-sectional view of an inflatable oropharyngeal glove 30 in accordance with another representative embodiment in its uninstalled state with a generally tubular portion 31 of a rigid bronchoscope inserted through an opening 32 formed in a proximal end 33 of the oropharyngeal glove 30. In FIG. 5, although the oropharyngeal glove 30 is shown in its uninstalled state, it is shown inflated to demonstrate its shape when it is in the inflated state. However, the oropharyngeal glove 30 will be installed in the patient's throat and mouth when it is in a deflated state. In the deflated state, the oropharyngeal glove 30 can be compressed into a suitable compressed shape for insertion into the patient's mouth and throat.

Once the oropharyngeal glove 30 has been installed, air or another suitable gas supplied via a first tube 35 is carried via a first conduit 36 through the wall of the first membrane portion 37 of the oropharyngeal glove 30 to a first pocket 38 disposed in the wall of the second membrane portion 39. This causes the second membrane portion 39 to insufflate, which causes the circumference of the second membrane portion 39 to expand, i.e., to widen. Air or another suitable gas supplied via a second tube 41 is supplied to a second pocket 42 disposed in the wall of the first membrane portion 37. This causes the first membrane portion 37 to insufflate, which causes the circumference of the first membrane portion 37 to expand, i.e., to widen. Widening the first and second membrane portions 37 and 39, respectively, in this manner causes the first and second membrane portions 37 and 39, respectively, to conform the inner surfaces of the mouth and throat, respectively, to create an airtight, or nearly airtight, seal between these surfaces and the outer surfaces of the first and second membrane portions 37 and 39, respectively.

One of the benefits of the inflatable oropharyngeal glove 30 shown in FIG. 5 is that it can be installed or deployed without the need for a tool. Another benefit is that the oropharyngeal glove 30 will work with patients of different sizes because the amount to which the oropharyngeal glove 30 is inflated can be controlled to ensure that the oropharyngeal glove 30 is inflated to the correct size to fit the patient's mouth and throat. In other words, for smaller patients, the oropharyngeal glove 30 will be inflated to a lesser degree than for larger patients. As with the oropharyngeal glove 1 shown in FIGS. 1-4, the oropharyngeal glove 30 can be made of any suitable material (e.g., medical-grade plastic and/or synthetic rubber) and can be made by any suitable process (e.g., molding).

Figure 6:
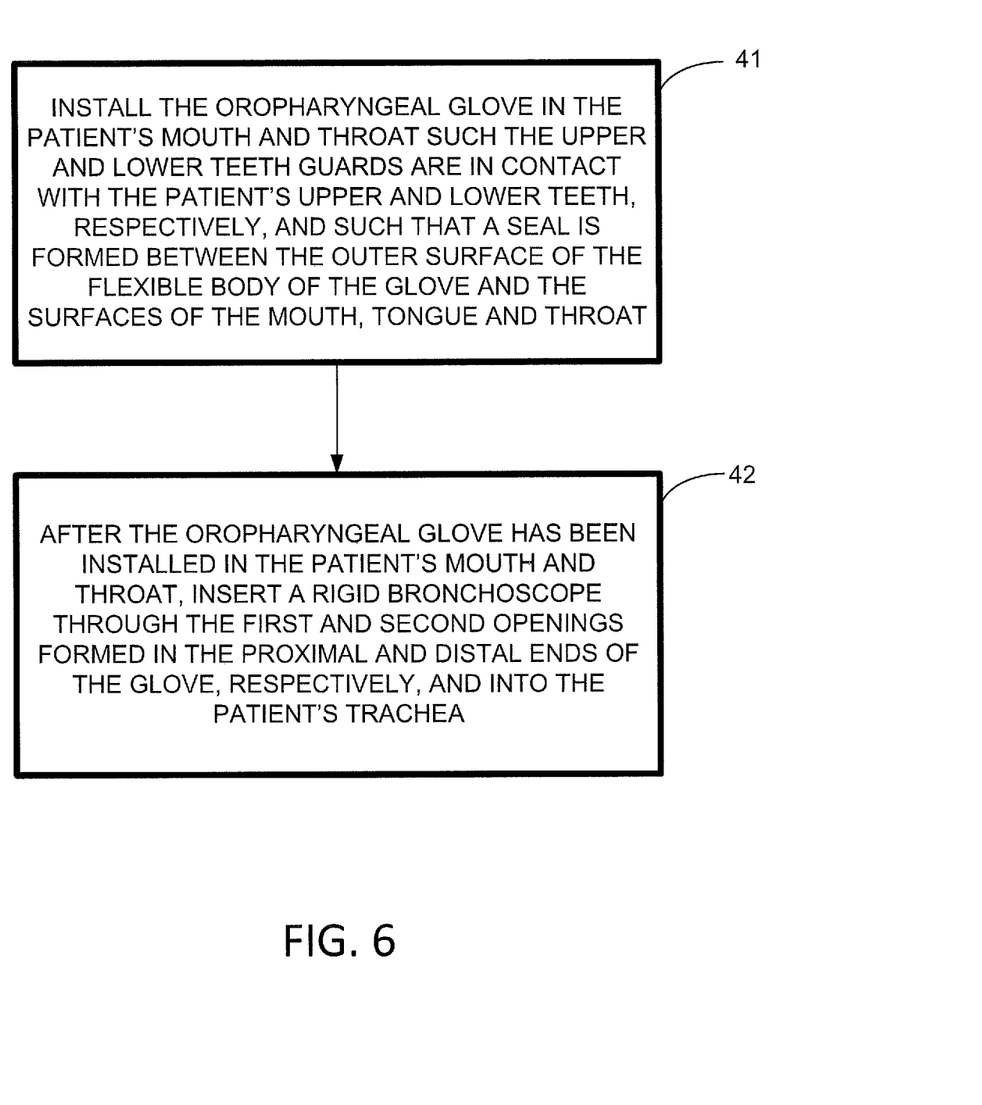
FIG. 6 illustrates a flow diagram of the method, in accordance with a representative embodiment, for performing a rigid bronchoscopy procedure using the oropharyngeal glove shown in FIGS. 1-4.

The method, in accordance with a representative embodiment, for performing a rigid bronchoscopy procedure using the oropharyngeal glove 1 will now be described with reference to FIG. 6. The oropharyngeal glove 1 is installed in the patient's mouth and throat such that the upper and lower teeth guards 15 and 16, respectively, are in contact with the upper and lower teeth, respectively, and such that an airtight, or nearly airtight, seal is formed between the outer surface of the flexible body 20 and the surfaces of the mouth, tongue and throat, as indicated by block 41. After the oropharyngeal glove 1 has been installed, a generally tubular portion of the rigid bronchoscope is inserted through the first and second openings 4 and 7, respectively, and into the patient's trachea 13, as indicated by block 42. The oropharyngeal glove 1 protects the mouth, teeth and throat of the patient from being damaged by the bronchoscope.

Figure 7:
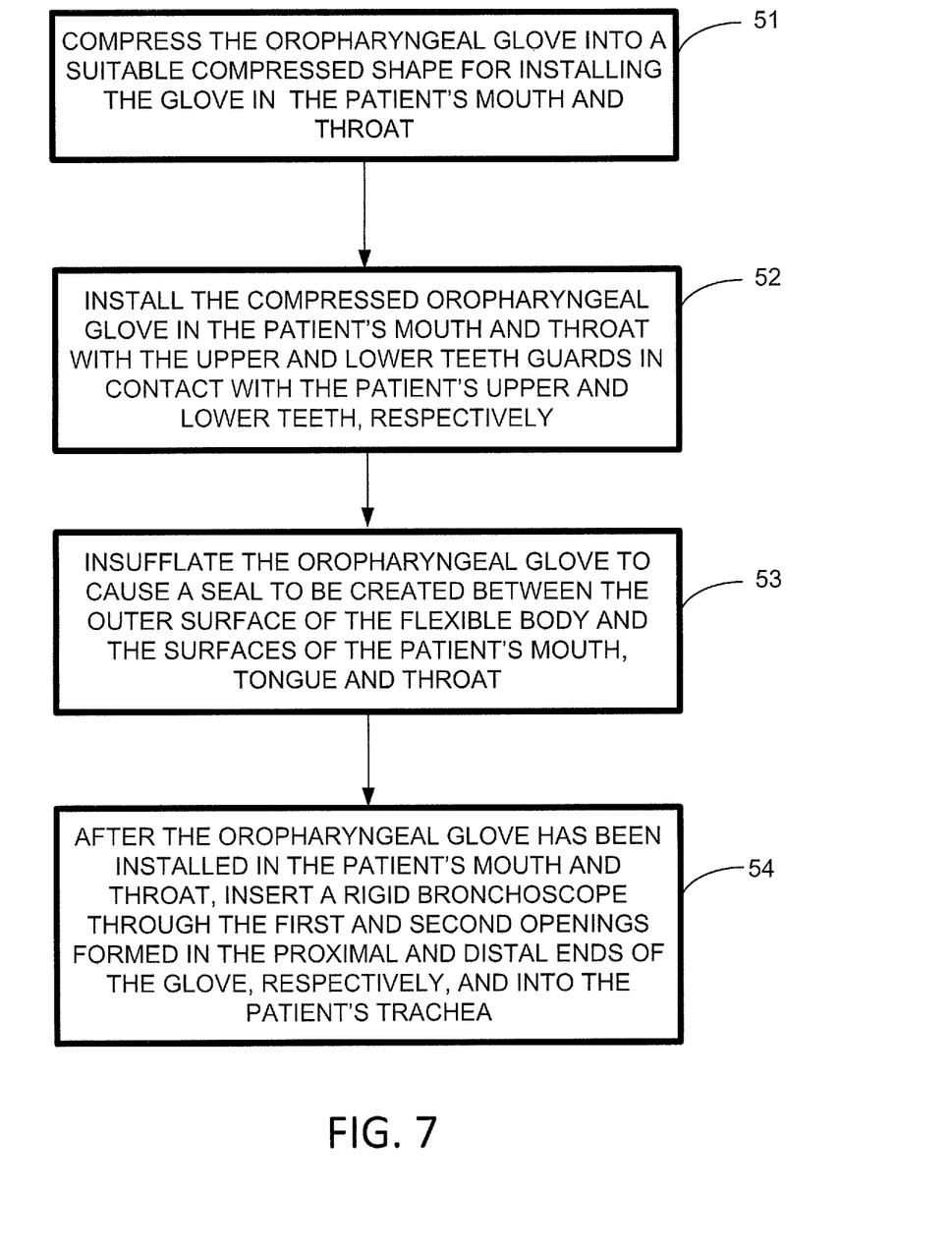
FIG. 7 illustrates a flow diagram of the method, in accordance with a representative embodiment, for performing a rigid bronchoscopy procedure using the oropharyngeal glove shown in FIG. 5.

The method, in accordance with another representative embodiment, for performing a rigid bronchoscopy procedure using the oropharyngeal glove 30 will now be described with reference to FIG. 7. The oropharyngeal glove 30 is compressed into a suitable compressed shape and installed in the patient's mouth and throat, as indicated by block 51. The oropharyngeal glove 1 is installed in the patient's mouth and throat with the upper and lower teeth guards 45 and 46, respectively, in contact with the upper and lower teeth, respectively, as indicated by block 52. The oropharyngeal glove 30 is then insufflated to cause an airtight, or nearly airtight, seal to be formed between the outer surface of the flexible body 47 of the oropharyngeal glove 30 and the surfaces of the mouth, tongue and throat, as indicated by block 53. After the oropharyngeal glove 30 has been installed in this manner, a generally tubular portion of the rigid bronchoscope is inserted through the first and second openings 32 and 48, respectively, and into the patient's trachea 13, as indicated by block 54. The oropharyngeal glove 30 protects the mouth, teeth and throat of the patient from being damaged by the bronchoscope.

It should be noted that the inventive principles and concepts have been described with reference to representative embodiments, but that the inventive principles and concepts are not limited to the representative embodiments described herein. Although the inventive principles and concepts have been illustrated and described in detail in the drawings and in the foregoing description, such illustration and description are to be considered illustrative or exemplary and not restrictive; the invention is not limited to the disclosed embodiments. Other variations to the disclosed embodiments can be understood and effected by those skilled in the art, from a study of the drawings, the disclosure, and the appended claims.

What is claimed is:

1. An oropharyngeal glove configured for use with a rigid bronchoscope that is passed through the oropharyngeal glove into a patient's trachea during a bronchoscopy procedure, the oropharyngeal glove comprising:
   a proximal end and a distal end, the proximal end having a first opening therein, the distal end having a second opening therein;
   upper and lower teeth guards disposed at the proximal end and partially defining the first opening;
   and wherein the oropharyngeal glove is configured as a flexible body extending from the upper and lower teeth guards to the distal end, the flexible body being configured to conform to a patient's mouth and throat when the oropharyngeal glove is installed in a patient's mouth and throat such that outer walls of the flexible body are in contact with features of the patient's mouth and throat, wherein the flexible body is configured to form a seal with the features of the patient's mouth and throat with which the flexible body is in contact, wherein the seal is configured to prevent or reduce air leakage from the patient's trachea, wherein the oropharyngeal glove protects the patient's mouth, teeth and throat from being damaged by the rigid bronchoscope, and wherein the flexible body is configured for the rigid bronchoscope to pass therethrough.

2. The oropharyngeal glove of claim 1, wherein the flexible body comprises a first membrane portion and a second membrane portion, the first membrane portion having a first end that joins the upper and lower teeth guards and having a second end that joins a first end of the second membrane portion, the second membrane portion having a second end that extends to the second opening formed in the distal end of the oropharyngeal glove, wherein when the oropharyngeal glove is installed in the patient's mouth and throat, outer walls of the first membrane portion are in contact with the patient's tongue, with inner walls of cheeks of the patient and with a roof of the patient's mouth, wherein when the oropharyngeal glove is installed in the patient's mouth and throat, outer walls of the second membrane portion are in contact with the patient's throat.

3. The oropharyngeal glove of claim 2, wherein the first membrane portion has a circumference that is greater than a circumference of the second membrane portion.

4. The oropharyngeal glove of claim 2, wherein the oropharyngeal glove is an integrally-formed part.

5. The oropharyngeal glove of claim 2, wherein the oropharyngeal glove comprises a medical-grade plastic material.

6. The oropharyngeal glove of claim 5, wherein the medical-grade plastic material is thickest in the upper and lower teeth guards and thinnest in the second membrane portion.

7. The oropharyngeal glove of claim 6, wherein the medical-grade plastic material is of greater thickness in the first membrane portion than in the second membrane portion.

8. The oropharyngeal glove of claim 2, wherein the oropharyngeal glove comprises a rubber material.

9. The oropharyngeal glove of claim 2, wherein the oropharyngeal glove is made of one or more materials selected from the group consisting of plastic and rubber.

10. The oropharyngeal glove of claim 2, wherein the first and second membrane portions are made of different materials.

11. The oropharyngeal glove of claim 2, wherein the flexible body is an inflatable body that is inflated by introducing a gas into at least a first inner region of the flexible body through a first port of the flexible body, wherein inflating the flexible body creates the airtight, or nearly airtight, seal.

12. The oropharyngeal glove of claim 1, further comprising:
    at least a first oxygen port disposed at the proximal end of the oropharyngeal glove.

13. The oropharyngeal glove of claim 12, further comprising:
    at least a second oxygen port disposed at the distal end of the oropharyngeal glove, the first and second oxygen ports being in communication with one another via a conduit disposed in walls of the flexible body.

14. The oropharyngeal glove of claim 1, wherein the second opening is a slit opening.

15. The oropharyngeal glove of claim 1, wherein when the oropharyngeal glove is installed in a patient's mouth, the distal end of the oropharyngeal glove is positioned in between vocal cords of the patient and an epiglottis of the patient.

16. The oropharyngeal glove of claim 15, wherein when the oropharyngeal glove is installed in a patient's mouth and throat, the flexible body blocks an entryway to an esophagus of the patient.

17. A method for performing a rigid bronchoscopy procedure, the method comprising:
    installing an oropharyngeal glove in a patient's mouth and throat, the oropharyngeal glove comprising:
        a proximal end and a distal end, the proximal end having a first opening therein, the distal end having a second opening therein;
        upper and lower teeth guards disposed at the proximal end and partially defining the first opening, the upper and lower teeth guards being in contact with upper and lower front teeth, respectively, of the patient;
        and wherein the oropharyngeal glove is configured as a flexible body extending from the upper and lower teeth guards to the distal end, outer walls of the flexible body being in contact with features of the mouth and throat of the patient, wherein the flexible body forms seal with the features of the patient's mouth and throat with which the flexible body is in contact that prevents or reduces air leakage from the patient's trachea; and
    inserting a rigid bronchoscope through the first and second openings and into a trachea of the patient, wherein the oropharyngeal glove protects the mouth, throat and teeth of the patient from being damaged by the rigid bronchoscope.

18. A method for performing a rigid bronchoscopy procedure, the method comprising:
    compressing an oropharyngeal glove into a suitable compressed shape for installing the oropharyngeal glove in a patient's mouth and throat;
    installing the compressed oropharyngeal glove in the patient's mouth and throat, the oropharyngeal glove comprising:
        a proximal end and a distal end, the proximal end having a first opening therein, the distal end having a second opening therein;
        upper and lower teeth guards disposed at the proximal end and partially defining the first opening, the upper and lower teeth guards being in contact with upper and lower front teeth, respectively, of the patient;
        wherein the oropharyngeal glove is configured as a flexible body extending from the upper and lower teeth guards to the distal end, an outer surface of the flexible body being in contact with features of the mouth and throat of the patient;
    insufflating the oropharyngeal glove to cause a seal to be created between the outer surface of the flexible body and the patient's mouth and throat, wherein the insuflated flexible body forms a seal with the features of the patient's mouth and throat with which the flexible body is in contact that prevents or reduces air leakage from the patient's trachea; and
    inserting a rigid bronchoscope through the first and second openings and into a trachea of the patient, wherein the oropharyngeal glove protects the mouth, throat and teeth of the patient from being damaged by the rigid bronchoscope.

* * * * *